(12) United States Patent
Gonzalez Herrera

(10) Patent No.: US 11,684,592 B2
(45) Date of Patent: Jun. 27, 2023

(54) MULTIRESISTANT-TUMOUR SENSITISER

(71) Applicant: Instituto Nacional de Neurologia Y Neurocirugia Manuel Velasco Suarez, Mexico City (MX)

(72) Inventor: Irma Gabriela Gonzalez Herrera, Mexico City (MX)

(73) Assignee: Instituto Nacional de Neurologia Y Neurocirugia Manuel Velasco Suarez, Mexico City (MX)

(*) Notice: Subject to any disclaimer, the term of this patent is extended or adjusted under 35 U.S.C. 154(b) by 314 days.

(21) Appl. No.: 16/629,125

(22) PCT Filed: Jul. 6, 2018

(86) PCT No.: PCT/MX2018/000065
§ 371 (c)(1),
(2) Date: Jan. 7, 2020

(87) PCT Pub. No.: WO2019/009693
PCT Pub. Date: Jan. 10, 2019

(65) Prior Publication Data
US 2020/0129451 A1    Apr. 30, 2020

(30) Foreign Application Priority Data
Jul. 7, 2017 (MX) .................... MX/a/2017/008989

(51) Int. Cl.
*A61K 31/12* (2006.01)
*A61P 35/04* (2006.01)
*A61K 31/495* (2006.01)
*A61K 9/00* (2006.01)

(52) U.S. Cl.
CPC ............ *A61K 31/12* (2013.01); *A61K 31/495* (2013.01); *A61P 35/04* (2018.01); *A61K 9/0014* (2013.01); *A61K 9/0043* (2013.01); *A61K 9/0073* (2013.01)

(58) Field of Classification Search
CPC ...................................................... A61K 31/12
See application file for complete search history.

(56) References Cited

FOREIGN PATENT DOCUMENTS

MX    2015006734        11/2016
MX    2015006734 A1  *  11/2016

OTHER PUBLICATIONS

Sotiropoulou et al, Chemical approaches to targeting drug resistance in cancer stem cells, Drug Discovery Today, 19(10), 1547-1562 Oct. 2014.*
Landeros, J.M., et al. A two-step synthetic strategy to obtain a water-soluble derivative of curcumin with improved antioxidant capacity and in vitro cytotoxicity in C6 glioma cells. Material Science and Engineering C (Feb. 1, 2017), 71, 351-362.*
Landerso, JM, et al. A two-step synthetic strategy to obtain a water-soluble derivative of curcumin with improved antioxidant capacity and in vitro cytotoxicity in C6 glioma cells. Material Science and Engineering C, Feb. 1, 2017, 71, 351-362. DOI:10.1016.
Belmont-Bernal Fernando et al.: "Systematic Derivatization of Curcumin abd it Effects on Antooxidant Capacity anb Action Mechanism. Cyclic Voltammetry abnd DFT as Tools of Analysys", Chemistryselect, mWiley-V CH Velarg GMBH & Co. KGAA, DE, vol. 1. No. 16, Jan. 2016, pp. 5091-5098.
Johant Lakey-Beltia et al: "Assesment of Novel Curcumin Derivatives as Potent Inhibitors of Inflammation and Amyloid-[Beta] Aggregation in Alzheimer's Disece", Journal of Azzeimer's Disease, vol. 60, No. s1, Sep. 15, 2017, pges S59-S68.

* cited by examiner

*Primary Examiner* — Svetlana M Ivanova
(74) *Attorney, Agent, or Firm* — Defillo & Associates, Inc; Evelyn A. Defillo

(57) ABSTRACT

The present invention refers to the use of the compound Cur-[G-2]-OH as a sensitizing agent in a wide range of multidrug-resistant tumors, especially glioblastoma, which are characterized by overexpression of the Nrf2 pathway.

4 Claims, 10 Drawing Sheets

A)

B)

MULTIRESISTANT-TUMOUR SENSITISER

CROSS REFERENCE TO RELATED APPLICATION

This application is a national stage entry of PCT/MX2018/000065 filed Jul. 6, 2018, under the International Convention and claiming priority over Mexican Patent Application No. MX/a/2017/008989 filed Jul. 7, 2017.

FIELD OF INVENTION

The present invention is inserted into the fields of pharmacology and human health. In general the present invention refers the use of Cur-[G-2]-OH in the preparation of drugs and pharmaceutical formulations useful to sensitize various types of cancer resistant to chemotherapy and/or radiotherapy (multidrug-resistant), mainly glioblastoma, as well as the treatment of patients with various types of multidrug-resistant tumors with medicinal products containing Cur-[G-2]-OH as an active ingredient.

BACKGROUND OF THE INVENTION

In 2012 there were 14.1 million of new cases of cancer and 8.2 million of cancer deaths worldwide (Estimated Incidence, Mortality and Prevalence Worldwide in 2012. GLOBOCAN 2012 (IARC)).

In cancer, chemotherapy represents the backbone of treatment for many types of cancer at different stages of the disease. Cancer resistance to chemotherapy is the innate and/or acquired ability of cancer cells to evade the effects of chemotherapy and is one of the most pressing problems in cancer therapy because it results in therapeutic failure and eventually in the patient's death (Alfarouk et al. Cancer Cell Int (2015) 15:71).

A common feature of the most aggressive cancers is the resistance to conventional treatments such as radiation therapy, chemotherapy and some specific drugs and it is responsible for poor prognosis in these patients.

Among the tumors most prone to developing resistance are those of breast, ovary, prostate, metastatic melanoma, lung, colorectal, head and neck, esophagus, hepatocellular carcinoma and glioblastoma multiforme, of which excels glioblastoma multiforme being the most common primary brain tumor, characterized by rapid cell growth and great local spread, so it has the worst prognosis, in both adults and children (Das A. et al. Cancer. 2010 Jan. 1; 116(1):164-76). Inevitably, death quickly comes as a result of the local progression of the tumor and its recurrence (Gagliano N. et al. Anticancer Drugs. 2010; 21(2):140-50), and to this date, no patient diagnosed with glioblastoma has been cured (Lefranc F., Kiss R. Neurosurg Focus. 2006; 20 (3): E7), making it a deadly disease that continues to challenge all current therapeutic strategies.

Although several mechanisms have been involved in the acquisition of multiresistance by tumor cells (Pan S T. and al. Clin Exp Pharmacol Physiol. 2016 August; 43(8):723-37), recent evidence has profiled the signaling pathway dependent on the transcription factor Nrf2, as critical in this process (Gañán-Gómez I. et al. Free Radic Biol Med. 2013; 65:750-64; Bai X. et al. Drug Metab Rev. 2016; 20:1-27), because it has been found that this protein is over-expressed aberrantly in various cancers including prostate, ovarian, endometrium, breast, lung, pancreas, esophagus and more recently, melanoma and glioblastoma (Zhang P. et al. Mol Cancer Ther. 2010; 9(2):336-46; Shim G S. et al. Free Radic Biol Med. 2009; Jiang T. et al. Cancer Res. 2010; 70(13): 5486-96; Syu J P. et al. Oncotarget. 2016; 7(12):14659-72; Singh A. et al. Cancer Res. 200; 68(19):7975-84; Arlt A. et al. Oncogene. 2013; 32(40):4825-35; Yamamoto S. et al. Mol Cancer Res. 2014; 12(1):58-68; Rocha C R. et al. Oncotarget. 2016), being responsible for its chemo- and radio-resistance.

A number of works have demonstrated the relevance of Nrf2 in cell protection, considering itself as the main actor in the cellular antioxidant response (Sykiotis G P. and Bohmann D. Dev Cell. 2008; 14(1):76-85). It is generally assumed that, under basal conditions, the interaction of Nrf2 with Keap1 results in low levels of expression of genes whose promoter contains the antioxidant response element (ARE), which include, among others, the encoding genes of antioxidant enzymes, the thioredoxin system and many ATP-dependent drug flow pumps (Zhang M, et al. Bioscience Hypotheses 2009; 2(4):261-263).

Under conditions of oxidative or electrophilic stress, Nrf2 is release from Keap1, allowing its translocation to the nucleus, where it exerts its transcriptional function in genes with ARE sites (Itoh K. et al. Genes Dev. 1999 Jan. 1; 13(1):76-86). Once the action of Nrf2 is complete, the Keap1/Cul3 complex relocates the Nrf2 protein from the nucleus to the cytoplasm, where its proteasomal degradation occurs. (O'Connell M A. and Hayes J D. Biochem Soc Trans. 2015; 43(4): 687-9). However, it is known that in tumor cells these mechanisms do not operate in the same way, since in these cells occurs the chronic activation of Nrf2 that gives to them protection against a toxic and nutrient-devoid medium, and to at the cytotoxic effects of anti-carcinogenic agents (Shibata T. et al. Proc Natl Acad Sci USA. 2008; 105(36):13568-73, Bai X. et al. Drug Metab Rev. 2016; 20:1-27; Gañán-Gómez I. et al. Free Radic Biol Med. 2013; 65:750-64), although it is unknown how tumor cells maintain high levels of Nrf2.

In addition to Keap1, other proteins regulating the activity of Nrf2 have been described, among which stands out p62 (Sequestosome-1 protein p62/SQS™), a multifunctional cytoplastic protein, which acts as a scaffolding to direct other proteins and organelles towards the autophagic pathway (Jaramillo M C. And Zhang D. Genes and dev. 2013; 27: 2179-2191).

The p62 protein interacts directly with Keap1, so that it interferes with the formation of the Keap1-Nrf2 complex (Copple I M. et al. J Biol Chem. 2010; 285(22):16782-8), but also has an ARE site on its promoter (Jain A. et al. J Biol Chem. 2010; 285(29):22576-91), so that its expression is induced by oxidative stress in a manner dependent on Nrf2, leading to a retro-feeding regulation, where a higher expression of p62, could mean the increased nuclear activity of Nrf2.

It has been shown that there is a positive correlation between high levels of Nrf2 and p62 in the most aggressive cancers (Thompson H G. et al. Oncogene. 2003; 22(15): 2322-2333; Kitamura H. et al. Histopathology. 2006; 48(2): 157-161; Rolland P. et al. Endocr Relat Cancer. 2007; 14(1):73-80; Jain A. et al. J Biol Chem. 2010; 285(29): 22576-91; Inami Y. et al. J Cell Biol. 2011; 193(2):275-284; Inoue D. et al. Cancer Sci. 2012; 103(4):760-76; Galavotti S. et al. Oncogene. 2013; 32(6):699-712; Li L. et al. Cancer Cell. 2013; 24(6):738-750; Ellis R A. et al. J Invest Dermatol. 2014; 134(5):1476-8).

Because p62 is indispensable for the survival and proliferation of tumor cells, but not for normal cells, it is considered an ideal therapeutic target (Gabai V L and Shifrin V I. International Reviews of immunology. 2014; 33: 375-382), so the development of agents that decrease the expression of p62 and/or Nrf2 as a strategy to treat the most aggressive tumor types, is a current topic of great interest (Shibata T, et al. Proc Natl Acad Sci USA. 2008; 105(36):13568-73; Gabai V L. and Shifrin V I. International Reviews of immunology. 2014; 33: 375-382; Kansanen E, et al. Redox Biol. 2013; 1:45-9).

However, the development of inhibitors specific to the Nrf2 pathway has represented a great challenge, due to their structural similarity with other members of the bZIP protein family (Kansanen E. et al. Redox Biol. 2013; 1:45-9) so to date there are few effective inhibitors reported.

It has been postulated that antioxidants can function as sensitizing adjuvants to anti-tumor therapies (Santandreu F M. et al. Cell Physiol Biochem. 2008; 22 (5-6):757-68; Gagliano N. et al. Anticancer Drugs. 2010; 21(2):140-50), but its use for these purposes has not yet been possible. An example of these antioxidants is curcumin, which has anticancer and antioxidant activity (Rahman I. et al. Biochem Pharmacol. 2006; 72(11):1439-52; Kumar G. et al. Life Sci. 2016; 148:313-28), capable of causing apoptitic cell death in in vitro cancer cells, but not in their normal counterparts (HailN Jr. Free Radic Biol Med. 2008; 44(7):1382-93), however, until now, has not been possible exploited the therapeutic potential of curcumin, due to its hydrophobic nature, poor bioavailability and instability to temperature and physiological pH (Lin J K. et al. Biofactors 2000; 13: 153-158; Sharma R A. et al. Clin Cancer Res. 2004; 10: 6847-6854).

Several approaches have been attempted to achieve the therapeutic use of curcumin, using structural analogues of curcumin and carriers such as liposomes, nanoparticles, phospholipid complexes, and dendrimers. For example, U.S. Pat. Nos. 8,487,139 and 9,328,081 and the application patent US2012/0003177 and MX/a/2015/006734, describe curcumin derivatives with enhanced solubility and that are useful as anticancer agents. Likewise, Gamage and collaborators (Gamage N H. et al. 2016. J Nanomed Nanotechnol. 2016 August; 7(4)), Shi and collaborators (Shi W. et al. 2007 Org Lett. December 20; 9(26):5461-4) and Wang and collaborators (Wang L. et al. 2013. J Mater Sci Mater Med. September; 24(9):2137-44) describe curcumin analogues useful for the treatment of different types of cancer. The effectiveness of this type of compounds and strategies is yet to be tested in the clinical field. A current problem in cancer treatment is the presence of innate or acquired resistance in many types of tumors, which decreases the available therapeutic options. The sensitization strategies of therapy-resistant tumors are based on the use of a drug or agent to make cancer cells more susceptible to a second drug. The sensitization of tumors allows to restore the activity of the second drug and/or decrease its dose which leads to lower toxicity.

Although various sensitizing agents of tumors have been described, there is still a need for new compounds or medication schemes capable of sensitizing multidrug-resistant cancer cells in order to decrease the mortality of this type of tumor, mainly by glioblastoma, which is still considered to be an intractable tumor.

SUMMARY OF THE INVENTION

The present invention refers to the use of conjugate dendrimer-curcumin Cur-[G-2]-OH formula:

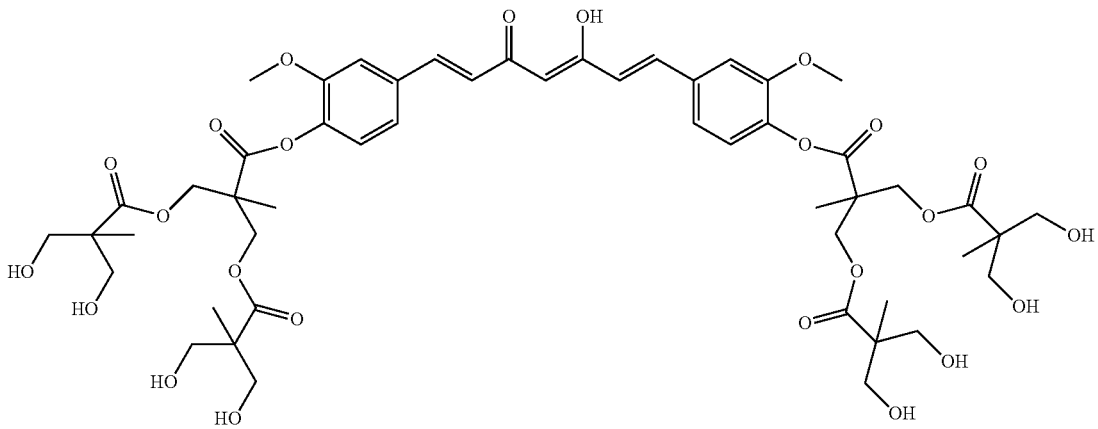 [SMILES: COc1cc(/C=C/C(=O)/C=C(O)/C=C/c2ccc(OC(=O)C(C)(COC(=O)C(C)(CO)CO)COC(=O)C(C)(CO)CO)c(OC)c2)ccc1OC(=O)C(C)(COC(=O)C(C)(CO)CO)COC(=O)C(C)(CO)CO]

as a sensitizing agent for multi-resistant tumors (chemical- and/or radio-resistant).

The modalities of the invention include the use of Cur-[G-2]-OH to prepare a drug or pharmaceutical formulation useful to increase sensitivity or decrease innate or acquired resistance of multidrug-resistant tumors and methods or treatment schemes of patients with multidrug-resistant tumors using a pharmaceutical drug or formulation that it includes Cur-[G-2]-OH to sensitize or decrease the innate or acquired resistance of such tumors and where Cur-[G-2]-OH is administered between 1 to 72 hours prior to conventional treatment administration.

DETAILED DESCRIPTION OF THE INVENTION

Figure 1:
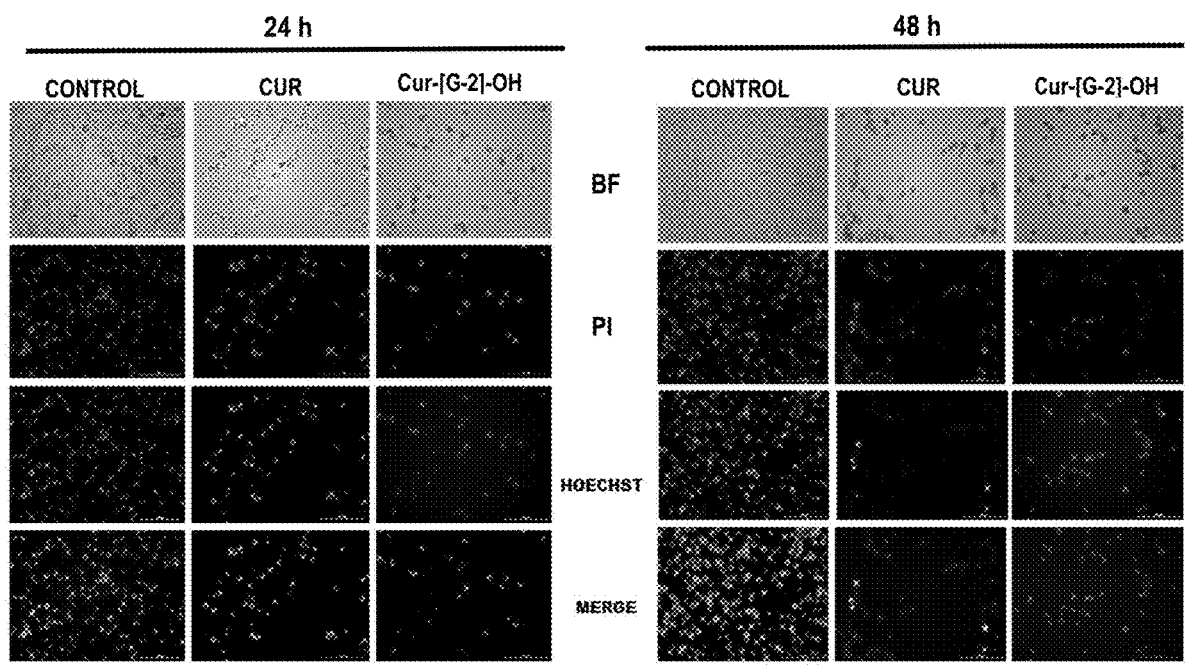
FIG. 1 shows the apoptotic cell detection assays using dual staining with propidium iodide (PI) and Hoechst 33342 (H) in C6 cells treated with curcumin 100 µM (CUR) or Cur-[G-2]-OH 300 µM for 24 and 48 hours. Images are shown in bright field microscopy (BFM), propidium iodide (PI) and Hoechst 33342 (Hoechst) separately and the overlap of both dyes (Merge). In cells treated with curcumin, all nuclei are observed stained with PI, while treatment with Cur-[G-2]-OH preserves the staining of the nuclei similar to that of untreated controls, even in later times (48 hours). 4× amplification.

Within the state of the art the properties and advantages of using curcumin as an anticancer agent are described, however, it is known that its bioavailability and stability under physiological conditions are not suitable for therapeutic use. Because of this, various forms of administration or release have been devised that allow curcumin to have an adequate physiological effect and, on the other hand, various curcumin derivatives have been developed with the aim of improving its solubility, stability in physiological conditions and bioavailability, while maintaining its anticancer properties and its specificity on tumor cells.

Cur-[G-2]-OH is a derivative of curcumin that has improved characteristics of solubility, stability and bioavailability with respect to curcumin, but which maintains an antioxidant and anticancer effect as good or better than that of curcumin.

Currently, the chemotherapy remains the backbone of treatment for many types of cancer, unfortunately, there are different types of tumors that have an innate or acquired resistance to these treatments leaving virtually no therapeutic options to patients who present it, which eventually causes his death due to the inability to stop tumor growth, so it remains highly desirable to have new medicines useful to sensitize or decrease the innate or acquired resistance of tumors resistant to conventional therapies, in order to improve the response to these types of treatments and decrease the mortality associated with multidrug-resistant tumours.

The present invention refers to a second use of the compound Cur-[G-2]-OH, as an agent that increases sensitivity or decreases the innate or acquired resistance of multiresistant tumors. Unexpectedly, it has been observed that, regardless of the anticancer effect that Cur-[G-2]-OH may have, this compound has the ability to sensitize or decrease the innate or acquired resistance of multidrug-resistant tumor cells, that is, improvement the response to treatment with conventional chemotherapeutic and/or radiotherapeutic agents, to which these cells were initially resistant, thus improving their effectiveness.

Also unexpectedly, it has been observed that this sensitizing effect or decrease innate or acquired resistance, from Cur-[G-2]-OH on multidrug-resistant cancer cells, occurs only if this compound is administered prior to administration of antitumor therapy, because its effect consists in the turning-off of the antioxidant response in these multidrug-resistant tumor cells through inhibition of the Nrf2 pathway.

The present invention overcomes the deficiencies of the state of the art by providing a new use of curcumin derivative Cur-[G-2]-OH, as a sensitizing agent, through the decrease to innate or acquired resistance of multidrug-resistant tumors, including glioblastoma, as well as new treatment schemes of multidrug-resistant tumors through administration of Cur-[G-2]-OH or pharmaceutical formulations comprising it, between 1 to 72 hours before administration of conventional therapy.

The present invention is based on the unexpected fact that Cur-[G-2]-OH, administered 1 to 72 hours before conventional therapy, is able to inhibit the Nrf2 pathway, lower the production of GSH and promote autophagy in multidrug-resistant cancer cells, which eliminates innate or acquired resistance from these types of tumors, even if they are sensitive to conventional treatment.

Previously, the direct antitumor activity of Cur-[G-2]-OH had been described, but the inventors of the present invention have developed a new use of this compound as a sensitizing agent, which allows to decrease the innate resistance or acquired of tumors multiresistant to conventional therapies.

As used in the description of this application, the term "multidrug-resistant tumor" refers to a malignant and aggressive tumor, which does not respond to conventional anticancer treatments, such as chemotherapeutic agents or ionizing radiation.

As used in the description of this application, the terms "sensitizer" and "sensitizer agent" refer to a compound, formulation or drug that has the ability to make multidrug-resistant tumor cells more sensitive to chemo- and/or radio-therapeutic agents, or to decrease the resistance of such tumor cells to agents. A "sensitizing agent" has the ability to improve the effectiveness of conventional treatment in tumors that are resistant to these types of treatments and can therefore be used as adjuvant therapy in the treatment of multidrug-resistant tumors.

The term "sensitize", as used in this description, refers to increasing sensitivity or decreasing the resistance of a multidrug-resistant tumor to conventional chemotherapeutic and/or radiotherapeutic agents. Terms such as sensitivity and sensitization are associated terms that refer to the effect that these sensitizing agents produce on multi-resistant tumors, improving their response to treatment with chemo- and/or radio-therapeutic agents.

As used in the description of this application, the term "conventional therapy" refers to the use, with the intention of reducing or eliminating tumors, of certain toxic chemical compounds, which can be classified as taxanes, camptothecin derivatives, platinum-based agents, nitrosoureas, anthracyclines and epipodophyllotoxins, used alone or in combination of two or more of them, and/or ionizing radiations. As an expert in the technical field may recognize, the terms "antitumor agent" or "anticancer agent" are similar terms that could describe a conventional cancer therapy, so these terms are used interchangeably within this application.

As an expert in the technical field at issue of the present invention may recognize, the term "glioblastoma" refers to the most common and deadly tumor among tumors of the Central Nervous System, of rapid growth, composed of a heterogeneous mixture of poorly differentiated astrocytic tumor cells, with pleomorphism, necrosis, vascular proliferation and frequent mitosis.

As an expert in the technical field at issue in the present invention may recognize, the term "therapeutically effective quantity" refers to the amount of an active compound that is necessary to obtain the desired therapeutic effect. In this particular case it refers to a sufficient amount of Cur-[G-2]-OH that is able to improve the sensitivity of tumor cells to conventional therapy.

For the development of the present invention, the first step was to elucidate the mechanism of action of Cur-[G2]-OH, for which the determination of apoptotic death by dual staining with propidium iodide and Hoechst was performed (Zanotto-Filho A. and al. J Nutr Biochem. 2012 June; 23(6):591-601) on rat glioma C6 cells (ATCC® CCL-107™). C6 cells treated with Cur-[G2]-OH quickly acquired a microscopic morphology different from curcumin treated cells, from the first hours after treatment, when there is still no cell death, and until late exposure times (FIG. 1).

Figure 2:
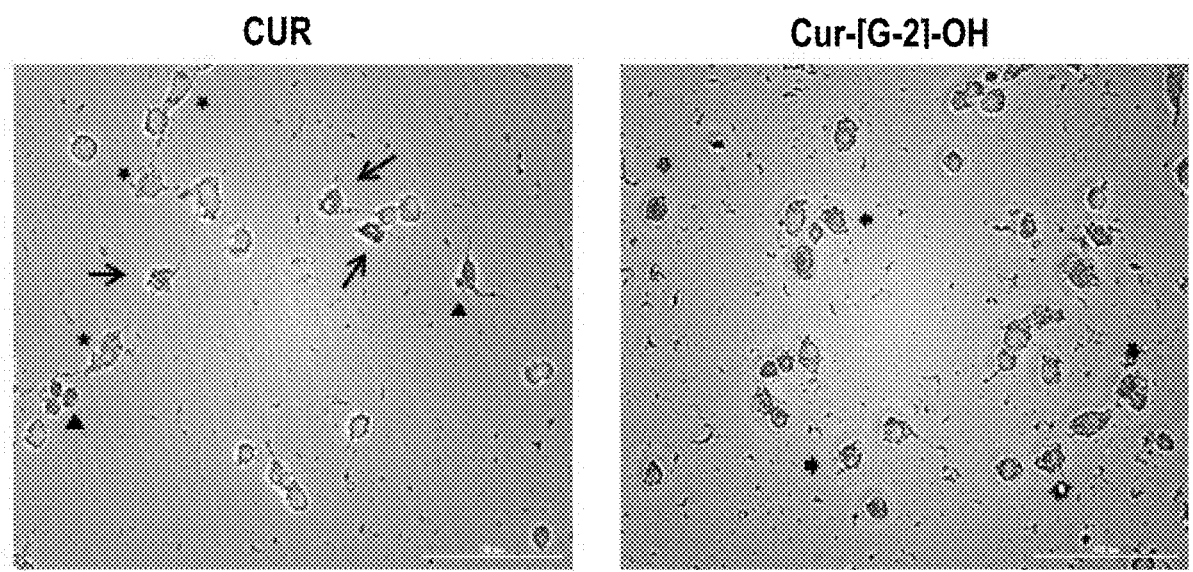
FIG. 2 shows the apoptotic cell detection assays by dual staining with propidium iodide (PI) and Hoechst 33342 (H) in C6 cells treated with curcumin 100 µM (CUR) or Cur-[G-2]-OH 300 µM at 20× amplification. Cells treated with curcumin show condensation of chromatin (stars), nuclear fragmentation (thin arrows) and apoptotic bodies (arrowheads), suggesting induction of apoptosis. Cells treated with Cur-[G-2]-OH have nuclei with relaxed chromatina and no PI staining (thick arrows).

Cells treated with curcumin exhibited chromatin condensation (stars), nuclear fragmentation (thin arrows) and apoptotic bodies (arrowheads) (FIG. 2), coinciding with multiple reports showing that apoptosis is the main type of cell death promoted by curcumin. On the other hand, the cells treated with Cur-[G-2]-OH retain a staining of the nuclei similar to that of the controls without treatment, with abundance of nuclei with relaxed chromatin (thick arrows) and without staining with propidium iodide (FIG. 2).

Likewise, a nuclear DNA fragmentation study was carried out by electrophoresis, observing that DNA fragmentation only occurs in cells treated with curcumin (FIG. 3), while in cells treated with Cur-[G-2]-OH, the DNA remains packaged and does not migrate in the gel. These results indicate that Cur-[G2]-OH has a different mechanism of action from apoptosis.

Once apoptosis was ruled out as a mechanism of action, the possibility of autophagy as a mechanism of action of the Cur-[G2]-OH was explored. For this purpose, the expression of autophagy markers in C6 cells treated with Cur-[G2]-OH was analyzed.

Figure 4:
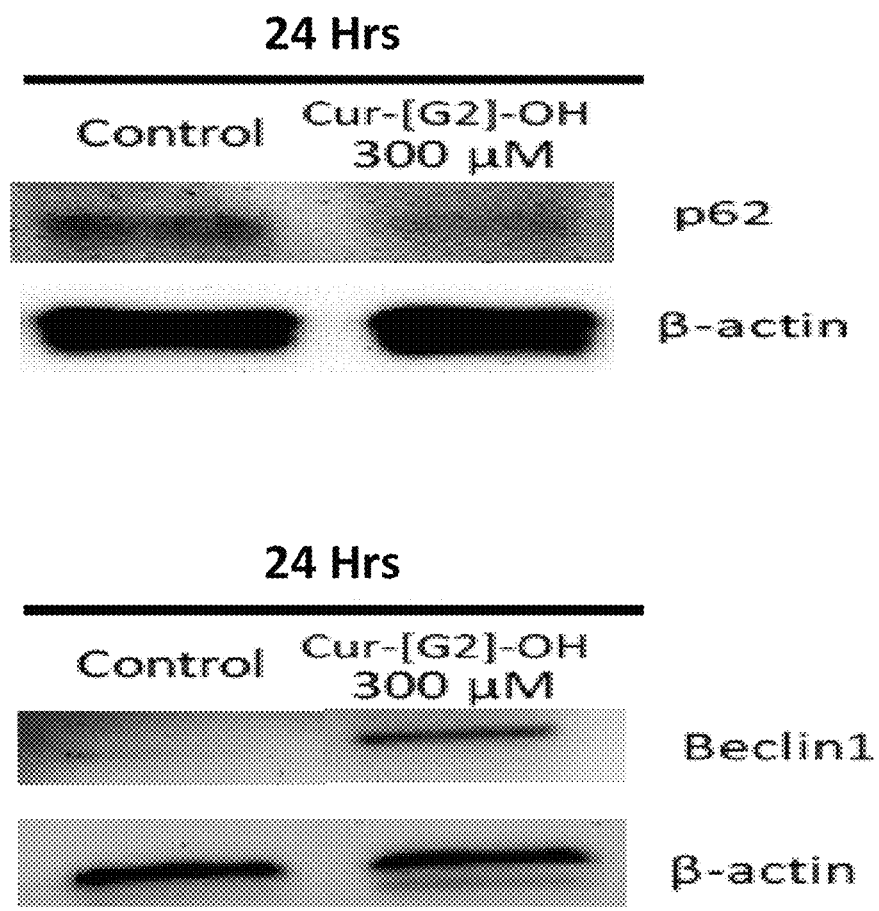
FIG. 4 shows the expression levels of the autophagy markers proteins p62 and Beclin1, using 40 μg of total proteins from C6 cells treated with Cur-[G2]-OH for 24 h and untreated C6 cells. Actin was used as loading control. The decrease in p62 expression and the increase in Beclin1 in cells treated with Cur-[G2]-OH compared to untreated cells is observed (20× amplification).
Figure 5:
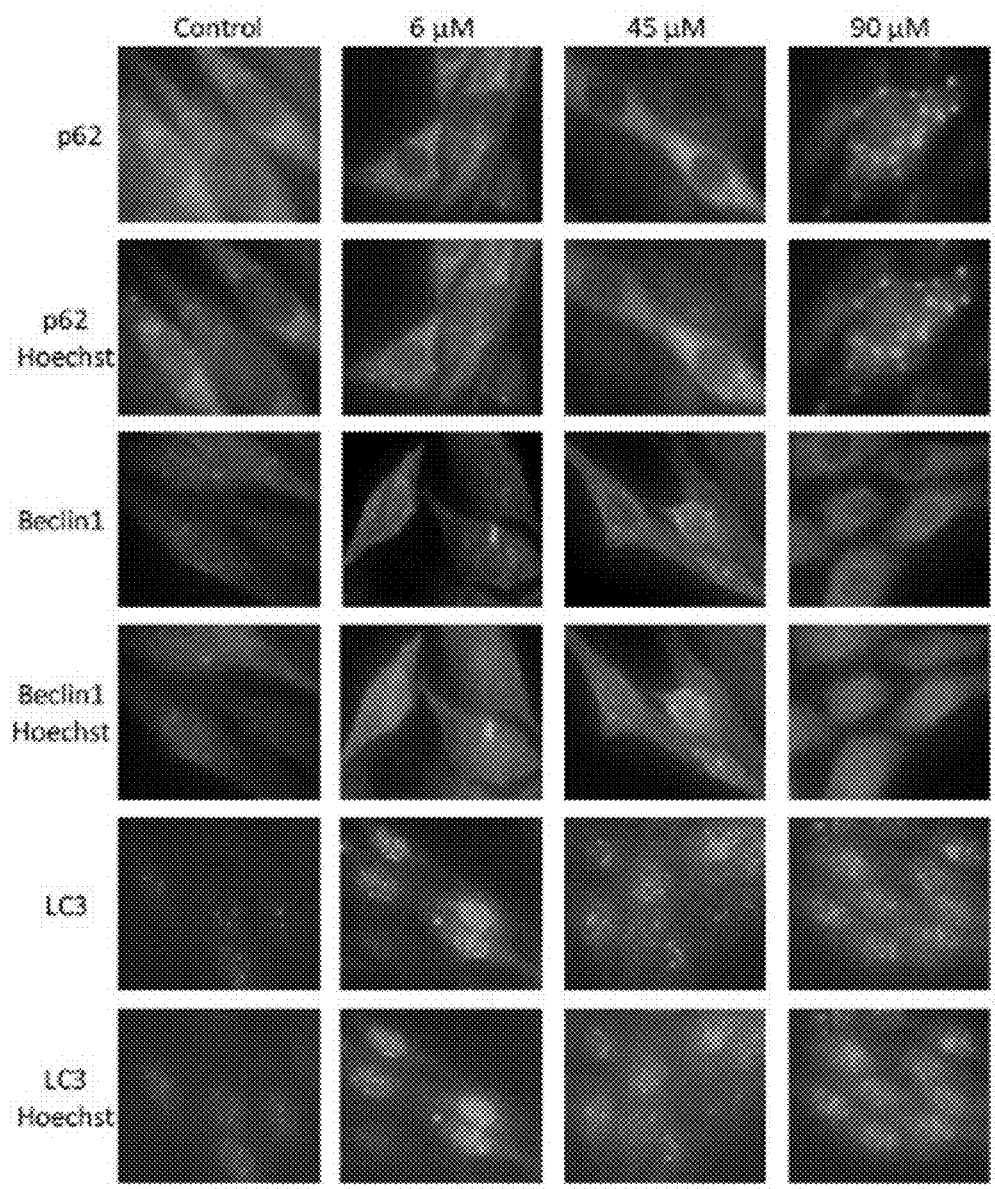
FIG. 5 shows micrographs (20×) representative of the expression levels of the autophagy markers proteins p62, Beclin1 and LC3 in C6 cells treated for 24 hours with different concentrations of Cur-[G2]-OH. Cur-[G2]-OH treatment induces increased expression and perinuclear accumulation of Beclin1. LC3 is detected in nuclear granules, and as the concentration of Cur-[G2]-OH increases, it is detected in the cytoplasm with the characteristic dotted pattern. Treatment with Cur-[G2]-OH decreases the expression of p62, particularly in the nucleus and with the greater concentrations of Cur-[G2]-OH, p62 is detected in cytoplasmic aggregates that form autophagosomes.

Treatment with Cur-[G2]-OH rapidly induces the increase in the expression of Beclin1 (FIG. 4) and LC3 proteins, which occurs as a function of time and the concentration of Cur-[G2]-OH (FIG. 5). Cur-[G2]-OH promotes perinuclear accumulation of Beclin1. Also, at low concentrations and in early times, it is observed that LC3 is strongly detected in nuclear granules, while as concentration and/or time increases, it is also detected in the cytoplasm with the characteristic dotted pattern.

Conversely, the protein p62, is strongly expressed in C6 cells (FIG. 4), with a nucleus-cytoplasmic distribution (FIG. 5). However, the treatment of these cells with Cur-[G2]-OH significantly decreases the expression of p62, particularly in the nucleus, even with very low concentrations (FIGS. 4 and 5). With the highest concentration and late times (from 24 hours), p62 is detected in the cytoplasmic aggregates that form the autophagosomes.

These results show that Cur-[G2]-OH induces cell death from autophagy, unlike curcumin that induces apoptosis.

p62 is a protein that participates in multiple signaling pathways, particularly in the regulation of the Nrf2 signaling pathway which has been implicated in the mechanisms of tumor resistance to conventional therapies. To determine the effect of Cur-[G2]-OH on p62 and the Nrf2 pathway, Nrf2 and Keap1 expression studies and Nrf2-p62, Keap1-p62 and Keap1-Nrf2 expression studies on C6 cells were performed with and without administration of Cur-[G2]-OH.

The results of these experiments demonstrated the presence of high basal levels of p62, Nrf2 and Keap1 in untreated C6 cells, all localized in both the nucleus and cytoplasm. Treatment with Cur-[G2]-OH rapidly induces the decrease in expression of Nrf2 in both the cytoplasm and the nucleus, even at low concentrations; unlike Keap1 which, although its expression is attenuated, significant levels are still detected, both in the nucleus and in the cytoplasm, with their expression being greater in the latter (FIG. 6).

Figure 6:
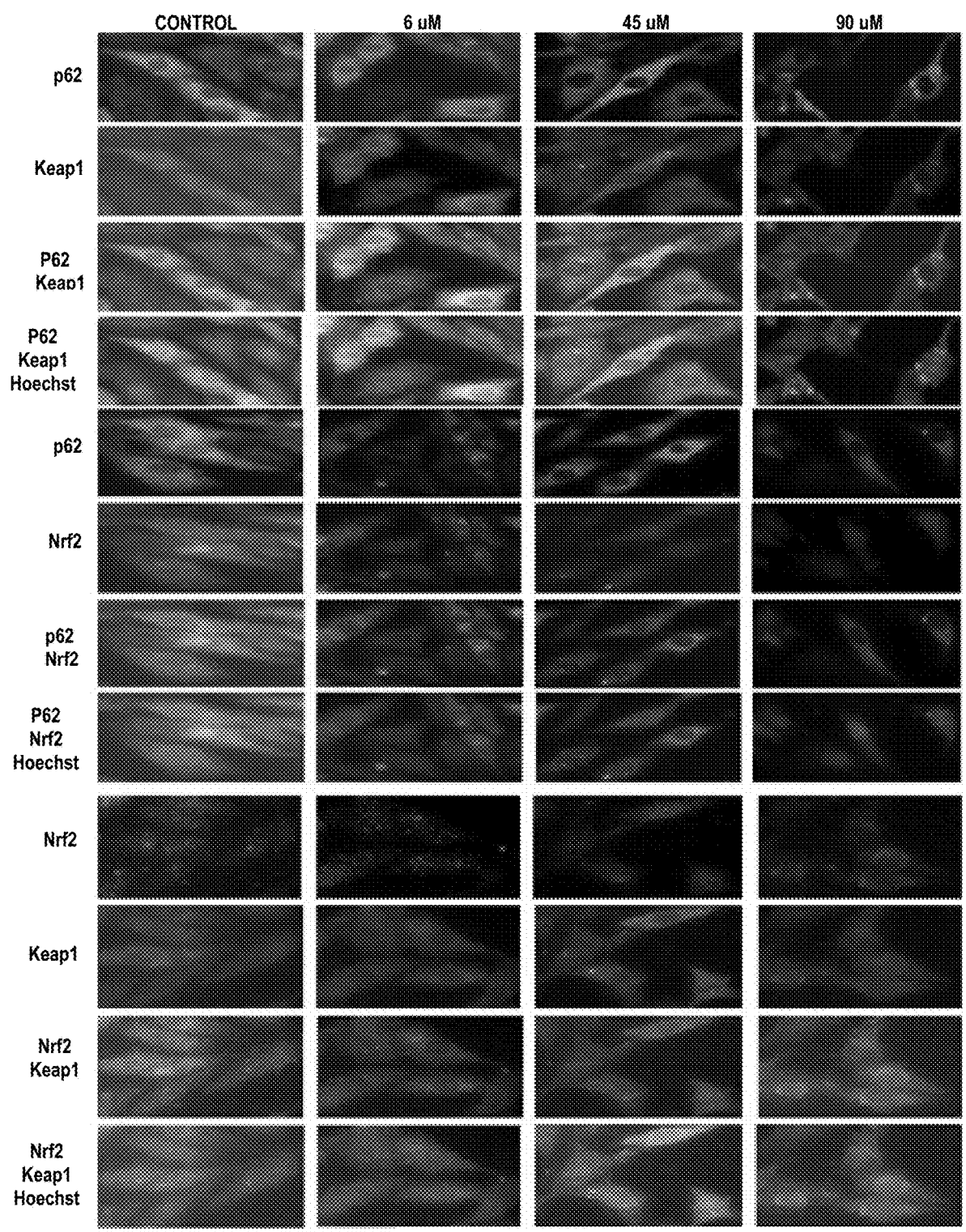
FIG. 6 shows the results of the expression studies of proteins Nrf2 and Keap1 and the co-location of Nrf2-p62, Keap1-p62 and Keap1-Nrf2 in C6 cells treated with different concentrations of Cur-[G2]-OH during 24 h and untreated C6 cells. The presence of high basal levels of proteins p62, Nrf2 and Keap1 is observed in untreated C6 cells, mainly in the nucleus. Treatment with Cur-[G2]-OH induces the loss of expression of Nrf2 in the cytoplasm and its attenuation in the nucleus while the expression of Keap1 is maintained, both in the nucleus and in the cytoplasm. The expression of p62 decreases in the nucleus and an interaction of Keap1 with Nrf2 in this subcellular compartment is observed, dependent of Cur-[G2]-OH concentration. The interaction of p62 with Keap1 is also observed in the cytoplasm and autophagosomes also in a Cur-[G2]-OH concentration dependent manner.

Colocalization studies showed that the exclusion of p62 from the nucleus is necessary for the interaction of Keap1 with Nrf2 in this subcellular compartment and that treatment with Cur-[G2]-OH promotes this mechanism, in a manner dependent on the concentration (FIG. 6). Simultaneously, Cur-[G2]-OH also promotes the interaction of p62 with Keap1 in the cytoplasm and in the autophagosomes (FIG. 6).

Treatment with Cur-[G2]-OH rapidly causes the decrease in Nrf2 expression in the cytoplasm (FIG. 6), which does not appear to be due to an increase in the degradation in the cytosol of Nrf2, since Keap1 is sequestered by p62, so one option was that Cur-[G2]-OH also interferes with de novo synthesis of Nrf2.

To test this hypothesis, the phosphorylation levels of the transcription factor eIF2-α, were analyzed, because the synthesis of Nrf2 in response to the various types of environmental stress is mediated by the p-eIF2/ATF4/Nrf2 axis, dependent on the stress of the endoplasmic reticle (Harding H P. et al. 2003. Mol Cell. 11:619-633; Zheng Q. Et al. 2014. Tumor Biol. 33:6255-6264; Cullan and Diehl. 2006. Int J Biochem Cell Biol.; 38(3):317-32).

Figure 7:
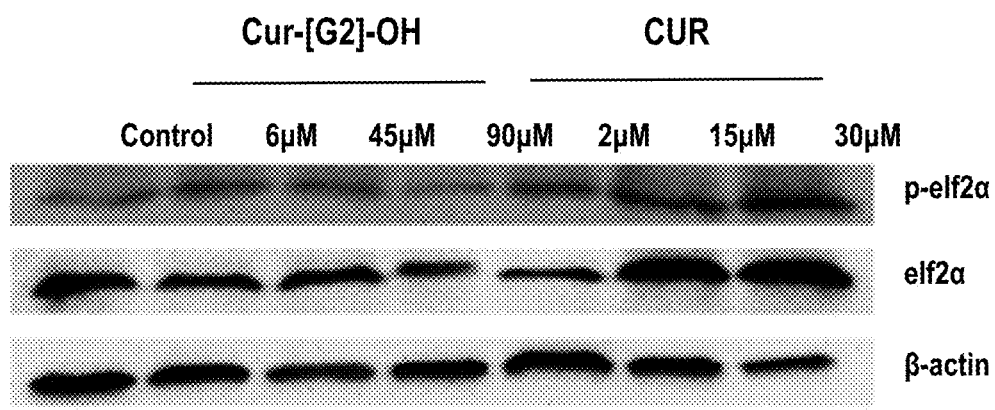
FIG. 7 shows the phosphorylation levels of transcription factor eIF2-α in cells treated with different concentrations of curcumin (CUR) and different concentrations of Cur-[G2]-OH for 24 h, as well as protein levels of Nrf2, in cells treated with Cur-[G2]-OH (300 μM), using the Immunoblot technique. A significant decrease in eIF2-α phosphorylation (p-eIF2-α) of is observed in cells treated with Cur-[G2]-OH, with no substantial changes in levels of total eIF2-α, while curcumin treatment increases both total eIF2-α and p-eIF2-α. Also, treatment with Cur-[G2]-OH causes a substantial decrease in Nrf2 protein levels when compared with untreated cells.
Figure 7:
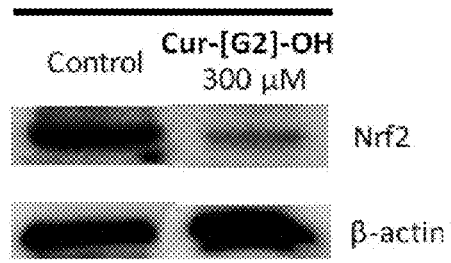

FIG. 7 shows a significant decrease in phosphorylation of eIF2-α before treatment with Cur-[G2]-OH, without substantial changes in the levels of total eIF2-α, which coincides with a significant decrease in Total levels of the Nrf2 protein, confirming the effect of this compound on the Nrf2 pathway. On the contrary, curcumin increases both the levels of total eIF2-α, and the levels of p-eIF2α, which suggests the coexistence of two mechanisms that are contrasted: on the one hand, the induction of apoptosis, and on the other, the synthesis of Nrf2.

Figure 8:
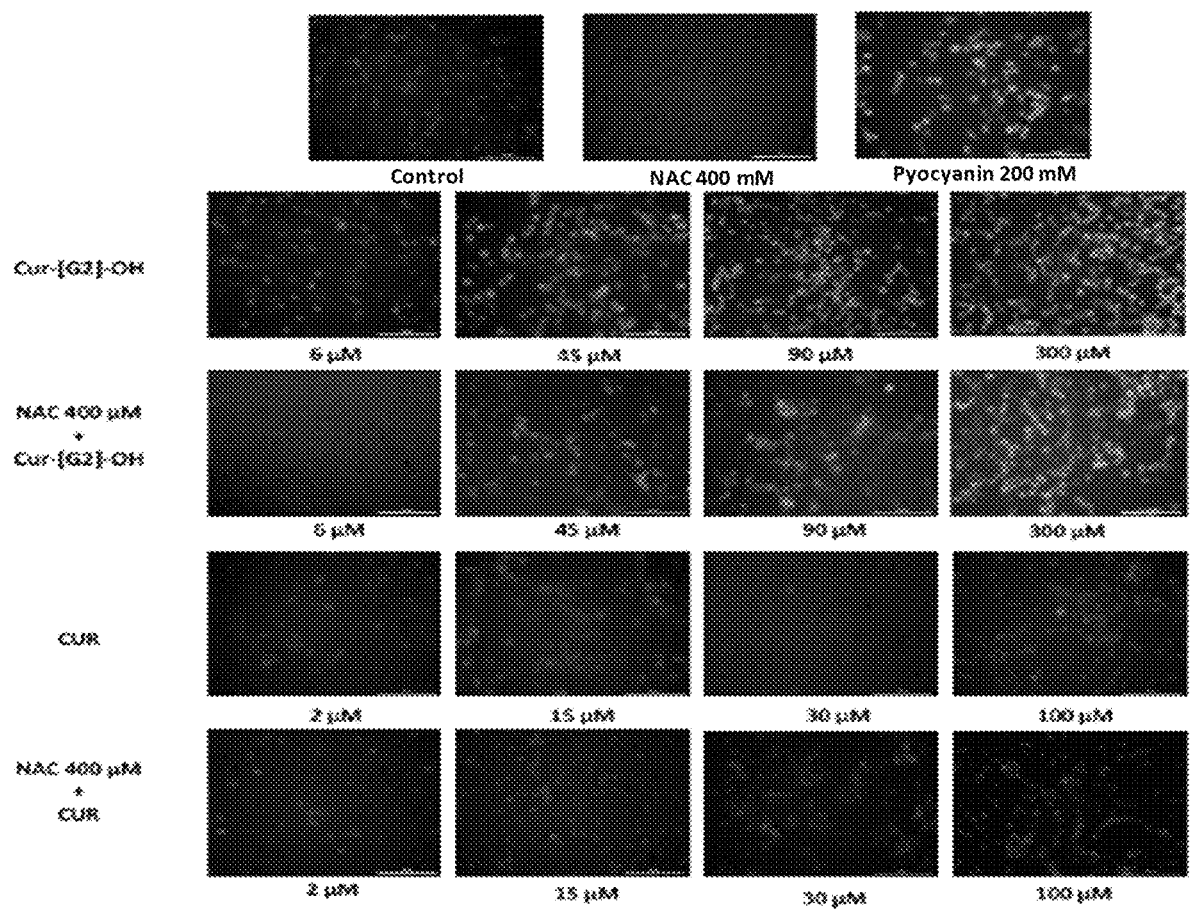
FIG. 8 shows the levels of Reactive Oxygen Species (ROS) in C6 cells treated with curcumin (CUR) and Cur-[G2]-OH in the presence and absence of N-acetyl Cysteine (NAC) for one hour. It is observed that Cur-[G2]-OH promotes the generation of ROS in a concentration-dependent manner, even in the presence of N-acetyl Cysteine (NAC), a specific inhibitor of ROS. Treatment with curcumin produce low amount of ROS and its effect is amplified with the use of NAC. As positive control a reactive species inducer (Pyocyanin) was used.

To confirm that the treatment with Cur-[G2]-OH turn off the antioxidant response, measurements of the levels of the Reactive Oxygen Species (ROS) were performed in C6 cells incubated with curcumin and with Cur-[G2]-OH. As seen in FIG. 8, in just one hour the Cur-[G2]-OH promotes the generation of ROS in a concentration-dependent manner, an effect that is slightly attenuated but not inhibited with the use of an antioxidant such as N-acetyl Cysteine (NAC), corroborating the lack of response by the Nrf2 pathway. In comparison, curcumin was much less effective in producing ROS and its effect is slightly amplified with the use of NAC, demonstrating that the mechanism of action of curcumin differs from the mechanism of action of Cur-[G2]-OH.

Several studies have shown that chronic exposure of tumor cells to different chemotherapeutic agents and ionizing radiation causes a selection of populations resistant to these agents, and an important mechanism for this phenomenon is the modulation of glutathione levels (GSH) by these populations, observing, for example, that the presence of glutathione plays an important role in the sensitization of neuroblastoma, ovarian cancer, acute lymphoblastic leukemia and other human cancers (Colla R. et al. Oncotarget. 2016 Oct. 25; 7 (43): 70715-70737).

It is also known that many of the drugs used in chemotherapy are activators of the Nrf2-dependent signaling pathway, which causes overexpression of the genes that contain the ARE sequences, including glutathione transferase enzymes, which leads to an elevation of the glutathione (Wang X J et al. Free Radic Biol Med. 2014 May; 70: 68-77), whose levels can be critical for extravascular growth of metastatic cells and tumor resistance in cancer cells. Given the above, it is thought that lowering glutathione levels in cancer cells may be a valid strategy to sensitize tumor cells to the effects of antitumor agents, or to prevent resistance to them (Traverso N. et al. Oxid Med Cell Longev. 2013; 2013: 972913).

Due to the importance of glutathione dependence for the processes of resistance of tumors to antineoplastic agents, experiments were conducted to determine variations in GSH concentration in C6 cells treated with different concentrations of Cur-[G2]-OH, with the aim of demonstrating the effect of treatment with this compound on glutathione levels and thus, on sensitization of multiresistant tumor cells.

Figure 9:
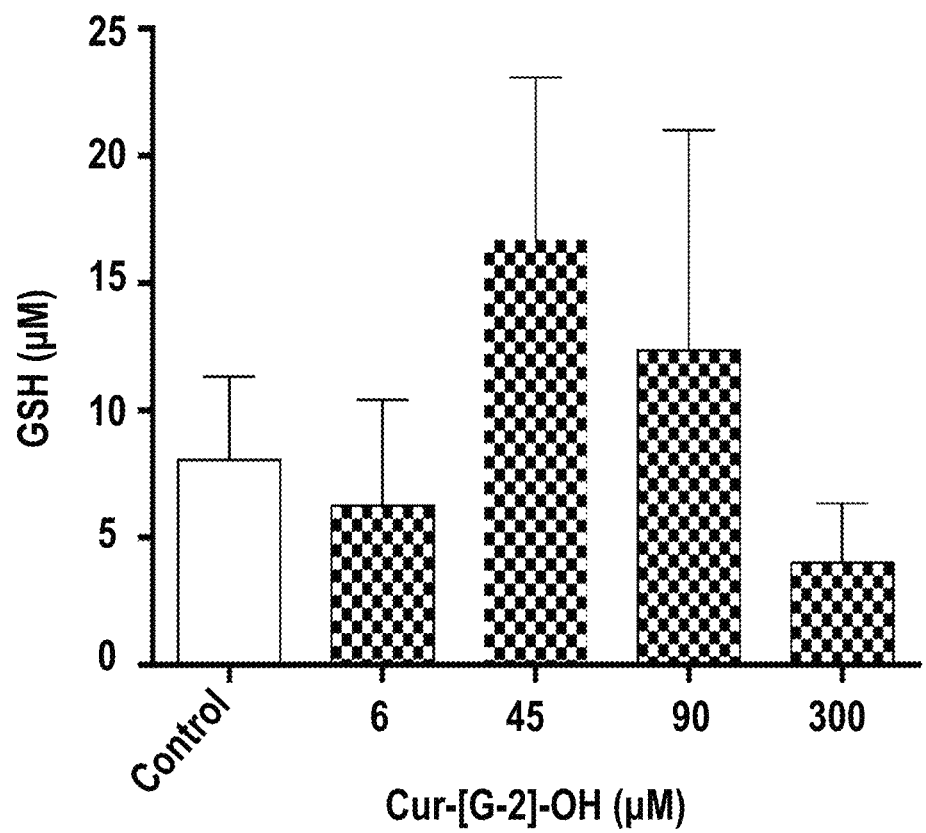
FIG. 9 shows the effect of Cur-[G2]-OH treatment on glutathione (GSH) concentrations in C6 cells. The cells were treated for 24 hours with different concentrations of Cur-[G2]-OH and GSH concentrations were measured using the GT10 colorimetric method (Oxford Biomedical Research®). Averages of 3 experiments (n=3) with standard deviation were plotted.

The results of these experiments (FIG. 9) show that Cur-[G2]-OH modulates levels of intracellular GSH in glioblastoma C6 cells, both dose and time dependent. The administration of intermediate doses of Cur-[G2]-OH (45 and 90 µM) in C6 cells induces a strong cellular response, which causes the baseline levels of GSH to increase considerably, coinciding with previous reports, which show that the mechanism of defense of tumor cells against damage caused by chemotherapeutic agents or radiotherapy is mediated by the modulation of GSH levels (Traverso N. et al. Oxid Med Cell Longev. 2013; 2013: 972913).

On the other hand, the administration of high doses of Cur-[G2]-OH (300 µM) caused a drastic decrease (about 50%) at GSH levels at 24 h, and the complete elimination of GSH levels is achieved at 48 hours at a concentration of 300 µM (data not shown). The use of high concentrations of Cur-[G2]-OH is not an inconvenience to its administration, since this compound is not toxic to normal cells at high concentration, which makes it a selective drug for tumor cells.

Considering the intracellular stability of Cur-[G2]-OH, this compound can be administered in several doses at short times, to achieve its intracellular accumulation and thereby achieve the complete elimination of GSH and improve the sensitization of multi-resistant tumors.

Finally, experiments were performed to demonstrate the effect of treatment with Cur-[G2]-OH on the sensitization of multidrug-resistant tumor cells, for example C6 glioblastoma cells, which are highly resistant to chemotherapeutic agents and radiotherapy. For these experiments, $FeSO_4$ was used as an oxidative stress inducing agent, in different administration schemes with Cur-[G2]-OH in C6 cells. $FeSO_4$ simulates intracellular redox conditions produced by various commonly used chemotherapeutic agents and by ionizing radiation.

Figure 10:
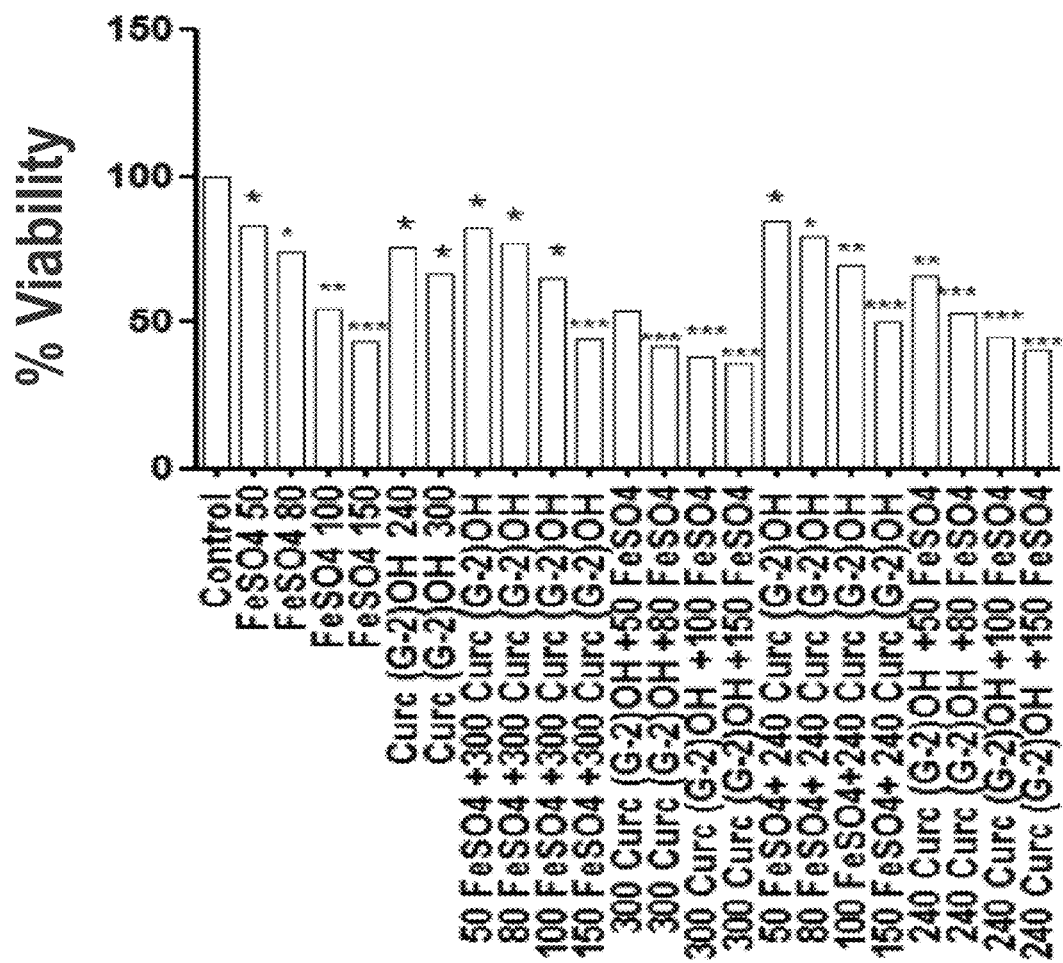
FIG. 10 shows the sensitization assays of glioblastoma C6 cells, resistant to oxidative stress, by treatment with Cur-[G2]-OH. The cells were incubated with different concentrations of $FeSO_4$, Cur-[G-2]-OH and combinations of both. In one modality, the cells were pre-incubated with $FeSO_4$ for 2 hours, and subsequently treatment with Cur-[G2]-OH was performed, incubating for 22 more hours ($FeSO_4$+Cur-[G2]-OH). In a second modality, the Cur-[G2]-OH was first added, incubating for 4 hours and subsequently the treatment with $FeSO_4$ was performed for additional 20 hours (Cur-[G2]-OH+$FeSO_4$). The percentage of cell viability with respect to the treatment of C6 cells with $FeSO_4$, Cur-[G2]-OH and the combination of both either pre-incubating with $FeSO_4$ and subsequently adding the Cur-[G2]-OH or vice versa is presented. Synergism is observed only between Cur-[G-2]-OH and $FeSO_4$ when cells are pre-incubated with Cur-[G-2]-OH and then $FeSO_4$ is added. The viability of untreated cells is considered as the 100%. $*p<0.05$, $p<0.01$, $*p<0.001$.

The results demonstrate the existence of a synergism between Cur-[G-2]-OH and $FeSO_4$, significantly reinforcing the cytotoxicity of both compounds, in a dose-dependent manner. Importantly, this effect is only achieved if C6 cells are previously incubated with the Cur-[G-2]-OH, allowing both the antioxidant response and the synthesis of GSH to be turned off, and then administer the $FeSO_4$. This synergism does not exist when cells are first exposed to $FeSO_4$ and then to Cur-[G-2]-OH, or when administered simultaneously, which clearly demonstrates that pre-treatment of tumor cells multi-resistant to Cur-[G-2]-OH sensitizes them to oxidative stress, which can be generated by the chemotherapeutic or radiotherapeutic agents used in conventional therapies (FIG. 10).

Another possible mechanism of action of the Cur-[G-2]-OH to reverse tumor multi-resistance, could be through inhibition of the expression of the protein Mrp1 (Multidrug-Resistance-Associated-Protein 1), which is key in the development of tumor tolerance to chemotherapy and is also dependent on the Nrf2-ARE pathway (Ji L. et al. PLoS One. 2013 May 7; 8(5): e63404).

According to the description made in this application, the invention refers to the use of the curcumin derivative Cur-[G-2]-OH formula:

In another preferred form of invention, Cur-[G-2]-OH is used to sensitize metastatic melanoma.

For the sensitizing effect of Cur-[G-2]-OH to be effective, this compound must be administered prior to administration of conventional therapy. In a modality of the invention, Cur-[G-2]-OH is administered between 1 to 72 hours before conventional therapy.

In a preferred modality of the invention, Cur-[G-2]-OH is administered 24 to 48 hours before conventional therapy.

In a modality of the invention, Cur-[G-2]-OH is administered between 1 to 72 hours before conventional therapy and its concentration is kept constant by administering several doses at short times, such as doses every 2 h, 4 h, 6 h, 8 h or 12 h.

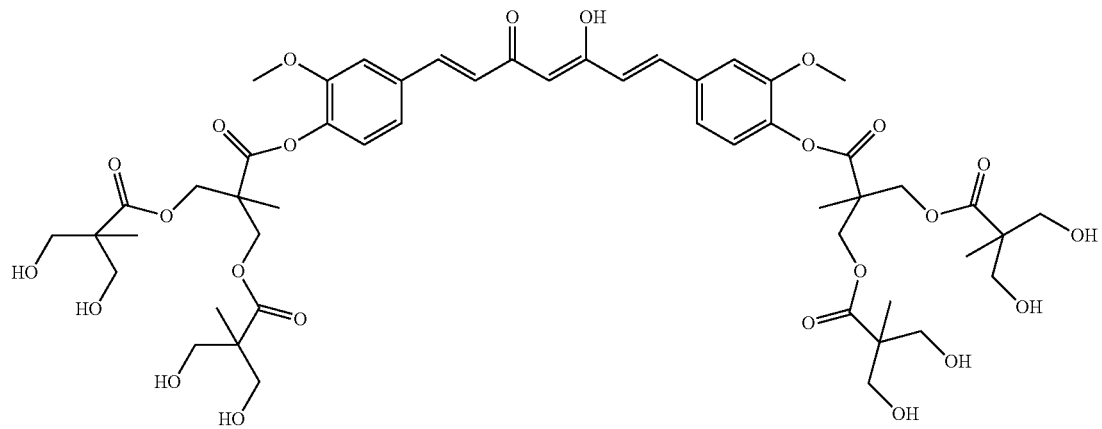 [SMILES: COc1cc(/C=C/C(=O)/C=C(O)/C=C/c2ccc(OC(=O)C(C)(COC(=O)C(C)(CO)CO)COC(=O)C(C)(CO)CO)c(OC)c2)ccc1OC(=O)C(C)(COC(=O)C(C)(CO)CO)COC(=O)C(C)(CO)CO]

to prepare a medicine useful to increase sensitivity or decrease innate or acquired to prepare a medicine useful to increase sensitivity or decrease innate or acquired resistance to conventional therapies in multidrug-resistant tumors in humans, mainly glioblastoma, where the compound is administered between 1 h and 72 h prior to administration of conventional therapy.

For the implementation of the present invention, the compound called Cur-[G-2]-OH can be used, as described in Landeros J M. et al. 2017. Mater Sci Eng C Mater Biol Appl. February 1; 71: 351-362 and in patent application MX20150006734, or any of its derivatives known in the state of the art. The aforementioned documents further describe the methods of obtaining or synthesizing Cur-[G-2]-OH.

Cur-[G-2]-OH may be combined with pharmaceutically acceptable excipients and optionally with sustained release matrices, such as biodegradable polymers, for example, to form therapeutic compositions by standard techniques known in the art.

To prepare the pharmaceutical compositions or formulations of Cur-[G-2]-OH, their pharmaceutically acceptable salts can be used, which can be prepared by any conventional methodology known in the technical field.

In a modality of the invention, multidrug-resistant cancer refers to any type of cancer resistant to conventional treatment, especially those characterized by overexpression of the Nrf2 pathway, among which are included without limitation: breast, ovary, prostate, lung, esophageal, colorectal, head and neck tumors as well as metastatic melanoma, hepatocellular carcinoma and glioblastoma multiforme.

In a preferred modality of the present invention the Cur-[G-2]-OH is used to sensitize glioblastoma multiforme.

In another modality of the invention, Cur-[G-2]-OH is administered between 1 to 72 hours before conventional therapy and the concentration of Cur-[G2]-OH is maintained constant by the administration of sustained doses at short times, but continued administration during one or several cycles of chemotherapy and/or radiotherapy.

Any antitumor therapy can be used for the application of the present invention after administration of Cur-[G-2]-OH. Particularly antitumor therapy refers to any type of cancer therapy based on the induction of oxidative stress, mainly those dependent on the Nrf2 pathway. Antitumor compounds that can be administered after sensitization with Cur-[G-2]-OH include, without limitation, placlitaxel, doxorubicin, cyclosporine A, daunorubicin, adriamycin, gemcitabine, ethoposide and temozolomide, in which it has been demonstrated that the associated resistance is due to the overexpression of the P-gp protein, which is mediated by the expression of the MRP-1 protein dependent on the Nrf2 pathway, in addition to the fact that curcuminoids have been observed to block the overexpression of P-gp (Xu D. et al. Mol Med Rep. 2013 January; 7 (1): 115-21). Another group of compounds that can be used are those in which it has been described that induces an overexpression of Nrf2 among those found without limiting verapamil, 5-flouracil, gemcitabine, doxorubicin, cyclophosphamide, valproic acid, temozolomide, anthracyclines, epirubicin, tamoxifen, radiotherapy, and platinum-derived compounds, such as cisplatin and oxaliplatin (Kang K A and Hyun J W Toxicol Res. 2017 January; 33 (1): 1-5).

In a preferred modality of the invention the antitumor compound that is administered after sensitization with cur-[G-2]-OH is temozolomide.

In a preferred modality of the invention conventional antitumor therapy that is administered after sensitization with Cur-[G-2]-OH is radiation therapy and temozolomide.

In another preferred modality of the invention the antitumor compound that is administered after sensitization with cur-[G-2]-OH is a compound derived from platinum.

In a preferred modality of the invention the multidrug-resistant tumor is glioblastoma multiforme and conventional therapy administered after sensitization with Cur-[G-2]-OH is radiation therapy and temozolomide.

The therapeutically effective dose of a compound, specific to any patient, will depend on a variety of factors that include the disorder being treated and its severity; the pharmaceutical formulation used; the age, body weight, health status, sex and diet of the patient; the time of administration, the route of administration and the rate of excretion of the compound; the duration of treatment; the drugs used in combination; and other similar factors well known in medical science, so that one skilled in the art will be able to establish at the time the appropriate dose to sensitize a patient with a multi-resistant tumor using the Cur-[G-2]-OH.

In a modality of the invention, Cur-[G-2]-OH is administered at doses between 5 and 500 mg/kg/day.

In a preferred modality of the invention, Cur-[G-2]-OH is administered at doses between 5 and 50 mg/kg/day.

In another preferred modality of the invention Cur-[G-2]-OH is administered at doses between 20 and 25 mg/kg/day.

The Cur-[G-2-OH can be adapted to create formulations suitable for oral, rectal, nasal, inhalation administration (McClure. R. et al. J Alzheimer's Dis. 2015; 44 (1): 283-95), topical (including dermal, transdermal, buccal and sublingual), vaginal or parenteral (including subcutaneous, intramuscular, intravenous, intraocular, intratracheal and epidural) according to the methods known in the state of the art. The formulations may conveniently be presented in unit dosage form and may be prepared by conventional pharmaceutical techniques known in the state of the art. Such techniques include the step of associating the active ingredient and a pharmaceutical carrier or excipient.

In the case of intranasal administration formulations, formulations in the form of nasal drops can be developed, to reach concentrations, for example between 50 and 500 mg/kg as described in Madane R. G. and Mahajan H. S. Drug Deliv. 2016 May; 23 (4): 1326-34, or formulations for atomization at concentrations of 0.5 to 2.5 mM/ml, for example, (McClure R. et al. J Alzheimer's Dis. 2015 Jan. 1; 44 (1): 283-295).

Formulations for intranasal application will generally be isotonic and may contain excipients to adjust or stabilize pH, between 6.4 and 6.8, a surfactant, such as Tween 80, for example, and a viscous agent, such as cellulose, arabic gum, alginate, pectins, vinyl polymers and acrylics, among others.

For formulations for intravenous administration, concentrations of 1 to 20 mg/kg may be used, for example, (Duan J. et al. Int J Pharm. 2010 Nov. 15; 400 (1-2):211-20). Because these preparations are intended for the administration of large volumes, it can be prepared as a sterile concentrated dilution, which prior to administration, is diluted in the final volume with an isotonic solution with blood.

In the case of formulations intended for oral administration, for example, concentrations of 50 to 200 mg/kg (Gal S. et al Chem Phys Lipids. 2007 December; 150 (2): 186-203) can be used. Due to the instability of Cur-[G-2]-OH in the acidic pH of gastric juices, it should be administered in the form of gastro-resistant delayed-release capsules, prepared to resist gastric juice and release the active substance in the intestinal fluid.

For formulations for topical administration, for example a hydrogel with concentrations of approximately 50 to 500 mg/ml (Li C. et al. Biomater Act. 2015. January; 11: 222-32). The formulation required for topical preparations is based on gelled liquids (hydrogel), whose bases are usually water, glycerol and propylengly glycol gelled with the help of appropriate gelling agents such as starch, cellulose derivatives, carbomers and magnesium and aluminum silicates, among others.

In a preferred modality of the present invention, the route of administration of Cur-[G-2]-OH or its pharmaceutical formulations is by inhalation.

In another preferred modality of the present invention, the route of administration is topically.

In another preferred modality of the present invention, the route of administration is parenteral.

In another modality, the invention refers to a method to increase the sensitivity of multidrug-resistant tumors, which includes: a) administering to a subject who needs it, a therapeutically effective amount of cur-[G-2]-OH, b) allow to pass between 1 and 72 hours after administration of Cur-[G-2]-OH and c) administer a chemotherapeutic or radiotherapeutic agent.

In a modality of the invention the multidrug-resistant tumor is selected from the group comprising: breast, ovary, prostate, lung, esophagus, colorectal, head and neck tumors, as well as metastatic melanoma, hepatocellular carcinoma and glioblastoma multiforme, among others, mainly those tumors are multidrug-resistant associated with overexpression of the Nrf2 pathway.

In a preferred modality of the invention the multidrug-resistant tumor is glioblastoma multiforme.

In another preferred modality of the invention the multi-drug-resistant tumor is metastatic melanoma.

In a preferred modality of the invention Cur-[G-2]-OH is administered between 1 h and 72 h before the chemotherapeutic or radiotherapeutic agent.

In another preferred modality of the invention Cur-[G-2]-OH is administered between 24 h and 48 h before the chemotherapeutic or radiotherapeutic agent.

In a preferred modality of the invention the chemotherapeutic agent is temozolomide.

In a preferred modality of the invention the chemotherapeutic agent is radiation therapy and temozolomide.

In a preferred modality of the invention the chemotherapeutic agent is a compound derived from platinum.

In a preferred modality of the invention the route of administration of the Cur-[G-2]-OH is by inhalation.

In a preferred modality of the invention the route of administration of the Cur-[G-2]-OH is topical.

In a preferred modality of the invention the route of administration of the Cur-[G-2]-OH is parenteral.

This invention is further illustrated by the following examples, which are not considered in any sense as limitations imposed on the scope of the claims. On the contrary, these examples are presented for a better understanding of the implementation of the invention, under the understanding that they only represent some of the modalities of the invention.

EXAMPLES

Example 1

Determination of the Mechanism of Action of Cur-[G2]-OH.

C6 cells from rat glioma (American Tissue Culture Collection, Rockville, Md., U.S.A. ATCC® CCL-107™) cultured under standard conditions in DMEM medium supplemented with Bovine Fetal Serum and 15% horse serum were used for the experiments. Because the molecular weight of curcumin (368 g/mol) is practically one third of the weight of Cur-[G2]-OH (1065 g/mol), and given that the chemical structure of Cur-[G2]-OH contains a curcumin core plus two second-generation dendrons, the experiments were performed using an equimolar ratio (1:3) in order to make the results between curcumin and Cur-[G2]-OH comparable.

Determination of Apoptotic Death by Dual Staining with Propidium Iodide and Hoechst 33342.

$1 \times 10^4$ C6 cells/well were cultured with 100 µl of Dulbecco's Modified Eagle's Medium (DMEM) medium for 24 hours in 96-well plates. The cells were treated with curcumin (100 µM), or with Cur-[G2]-OH (300 µM), or with the respective vehicle as a control. After 24- or 48-hours post-treatment, the cells were fixed with a mixture of methanol/acetone (1:1) and stained with propidium iodide (0.5 µg/ml), washed and Hoechst 33342 dye was added (0.1 µg/ml) for staining the nuclei. Cells were observed on the Cytation 3® plate reader (BioTek® Instruments, Inc.) using the DAPI ($\lambda$=377-447 nm) and Texas Red ($\lambda$=586-647 nm) filters, and the images were captured and analyzed with the Gen5 2.06® program.

Cells treated with Cur-[G-2]-OH have a staining of the nuclei similar to that of the untreated controls (FIG. 1), with abundant nuclei with relaxed chromatin and no staining with propidium iodide (thick arrows) (FIG. 2); while curcumin-treated cells exhibit chromatin condensation (stars), nuclear fragmentation (thin arrows) and apoptotic bodies (arrowheads) that indicate a mechanism of action mediated by apoptosis (FIG. 2).

DNA Fragmentation Assay

To determine DNA fragmentation, C6 cells ($1 \times 10^6$) were seeded in Petri dishes (100 mm) at a confluence of 70%. They were treated with curcumin (100 µM) or Cur-[G2]-OH (300 µM) and incubated for 24 and 48 hours. Controls were incubated with vehicle only (DMSO or PBS respectively).

The DNA was extracted using Trizol (Invitrogen® 15596-026), according to the supplier's specifications, and quantified on a spectrophotometer (Genesys 8®). 20 µg of DNA from each sample was deposited on a 1.5% agarose gel. Electrophoresis was performed at 100 V for 90 minutes. The gel was stained with the Hydragreen™ dye (ACTGene ACT-IDM604) and DNA detection was performed using the ethidium bromide filter and UV light on the Chemidoc-It TS2 imager photodocument (UVP, CA).

Figure 3:
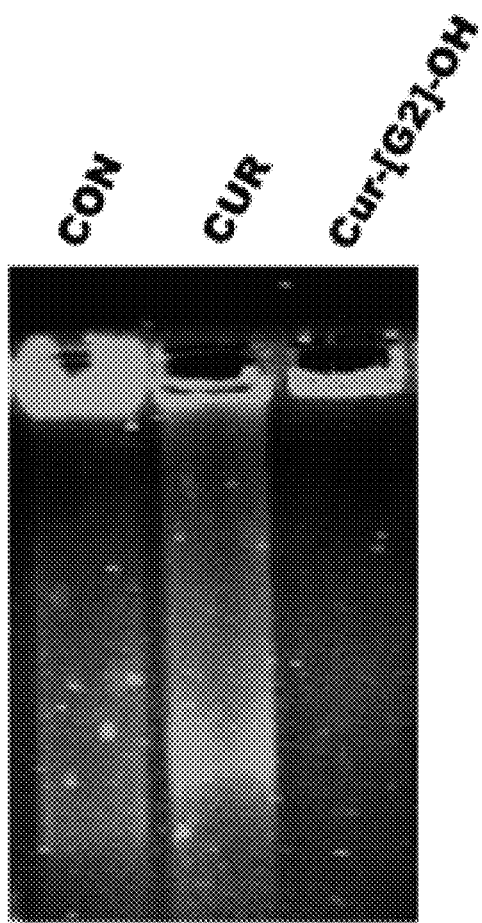
FIG. 3 shows DNA fragmentation studies in C6 cells treated with curcumin 100 μM (CUR) or Cur-[G2]-OH 300 μM for 24 h and control cells (CON). DNA fragmentation was only evident in cells treated with curcumin, while in cells treated with Cur-[G-2]-OH DNA remains packed and does not migrate into the gel.

DNA fragmentation was only evident in cells treated with curcumin, while in cells treated with Cur-[G-2]-OH, DNA remains packed and does not migrate into the gel (FIG. 3).

Analysis of Autophagy Markers and Nrf2 Pathway by Western Blot

C6 cells were grown in 25 $cm^2$ culture bottles (Corning® N.Y.) to form a 70% confluent monolayer (approximately $4 \times 10^6$ cells) and treated with Cur-[G2]-OH (300 µM) for 24 hours. The cells were washed in cold PBS, and lysis buffer (50 mM Tris-HCl, 120 mM NaCl, 0.01% IGEPAL) was added with a protease inhibitor cocktail (Sigma® P8340) and centrifuged to recover the supernatant. Proteins were quantified by the Lowry method (Lowry et al. 1951).

For the analysis of the proteins Beclin-1, p62, Nrf2, eIF2a and p-eIF2α, the treatments were performed with curcumin (2, 15 and 30 µM) or Cur-[G2]-OH (6, 45 and 90 µM) for 24 hours, proceeding to lysis cell with the RIPA Buffer with protease inhibitor (Sigma® P8340), NaF (5 mM) and Sodium Ortovanadate (1 mM), continuing with the same methodology above. 40 µg of proteins were resolved in 12% SDS-PAGE gels and transferred to Polyvinylidene Diflouride membrane (PVDF) (Immobilon® Millipore). The membranes were blocked with skim milk and subsequently incubated with the respective primary antibody (Beclin1, ab62557; p62, ab91526; Nrf2, sc-30915; p-eIF2α, sc-12412; eIF2, sc-11386 or β-actin, sc-47778) under stirring overnight at 4° C. After incubation, the membranes were washed with a Tween 20 tris-base saline buffer (TBST) and incubated with the respective secondary antibody conjugated to horseradish peroxidase (SIGMA). The bands were visualized by chemiluminescence with the Western Blotting Luminol Reagent reagents (Santacruz Biotechnology®), and the ChemiDoc-It® TS2 Imaging System (UVP, LLC).

It is observed that treatment with Cur-[G-2]-OH decreases the expression of p62 and increases the expression of Beclin1 (FIG. 4)

Analysis of Autophagy Markers and Nrf2 Pathway by Immunofluorescence

Simple staining: $1 \times 10^4$ C6 cells/well were cultured with 100 µL of DMEM medium in 96-well plates and incubated 24 hours. Cells were treated with different concentrations of Cur-[G2]-OH (3, 6, 15, 30, 45, 90 and 150 µM), and incubated for 6 and 24 hours. Control cells were replaced only with fresh DMEM medium. The cells were washed with cold PBS and fixed with a mixture of methanol/acetone (1:1) for 5 minutes; they were washed with PBS and incubated with 1% BSA in PBST. Subsequently, they were incubated with the primary antibody (p62, Beclin1 or LC3) at 4° C. overnight. They were washed and incubated with the fluorochrome-conjugated secondary antibody (Abcam® ab150073 Alexa fluor 488) for 1 hour at room temperature. They were washed with PBS and the nucleus stained with Hoechst 33342 (0.1 µg/ml). The images were observed on a Cytation 3® multimodal plate reader and captured and analyzed with the Gen5® 2.06 program using the DAPI ($\lambda$=377-447 nm) and GFP ($\lambda$=469-525 nm) filters.

It is observed that treatment with Cur-[G2]-OH induces the expression of proteins Beclin1 and LC3, in a concentration-dependent manner, while significantly decreasing expression of p62 occurs. Likewise, with the treatment with Cur-[G2]-OH the perinuclear accumulation of Beclin1 is promoted and it is observed that LC3 is strongly detected in nuclear granules, while as concentration and/or time is increased, it is also detected in the cytoplasm with the characteristic dot pattern, while p62 is detected in cytoplasmic aggregates that form the autophagosomes (FIG. 5).

Sequential immunofluorescence: For the protein co-location studies of Keap1-p62, Nrf2-p62 and Keap1-Nrf2, $5 \times 10^3$ C6 cells/well were grown in half-area 96 well plates and incubated for 24 hours. Subsequently, the cells were treated with Cur-[G2]-OH (6, 45 or 90 M) and incubated for 24 hours. In control cells only DMEM medium was replaced by fresh medium. Then, cells were washed with cold PBS and fixed with paraformaldehyde (4% in PBS) or with a mix of methanol/acetone, with paraformaldehyde, cells were washed and permeabilized with PBST (this step was not performed on the cells fixed with methanol/acetone). Cells were washed again and blocked in BSA at 1% in PBST.

The cells were incubated in the first primary antibody (Keap1 or Nrf2) at 4° C. overnight, and subsequently washed and re-incubated with the fluorochrome-conjugated secondary antibody (Alexa fluor 488 Abcam® ab150129), in the dark for 1 hour at room temperature. They were washed and again blocked for 30 minutes with goat serum; The serum was removed and the solution of the second respective primary antibody (p62 or Nrf2) was placed. It was incubated at 4° C. overnight. The incubation of the secondary antibodies proceeded in the same manner as described before, but using the Alexa flour 647 antibody from Abcam® (ab150079). The nuclei were stained with Hoechst 33342 solution (0.1 µg/ml) and the images were captured on a Cytation 3® multimodal plate reader (Bio Tek®, Instruments Inc.), with the Gen5 2.06 program using DAPI filters ($\lambda$=377-447 nm), GFP ($\lambda$=469-525 nm) and Texas Red ($\lambda$=586-647 nm).

The presence of high baseline levels of p62, Nrf2 and Keap1 is observed in untreated C6 cells, mainly in the nucleus. Treatment with Cur-[G2]-OH rapidly induces the loss of the expression of protein Nrf2 in the cytoplasm and the attenuation of the signal in the nucleus; unlike Keap1 that significant levels are still detected, both in the nucleus and in the cytoplasm, being greater its expression in the latter. It is also observed that treatment with Cur-[G2]-OH promotes the exclusion of p62 from the nucleus and its interaction with Keap1 in the cytoplasm and autophagosomes (FIG. 6).

Determination of Reactive Oxygen Species (ROS)

Intracellular generation of ROS was evaluated in real time by fluorescence microscopy using the ENZ-51011 detection kit (Enzo® Life Sciences). $5\times10^5$ cells per well were grown in half-area 96 wells plates (Costar 3595®) and incubated for 24 hours. Then, were incubated for 1 hour, with curcumin (2, 15, 30 or 100 µM), or Cur-[G2]-OH (6, 45, 90 or 300 µM) alone or in the presence of the ROS inhibitor N-Acetyl Cysteine (NAC, 400 µM) according to the manufacturer's instructions. As controls, pyocyanin (200 µM) was used as an inducer and NAC (400 M) as an inhibitor, or DMEM medium with or without DMSO as a negative control. At the end of treatment, the test solutions were withdrawn, and the ROS detection solution was added. The plates were observed under bright field and fluorescence microscopy with the GFP filter ($\lambda$=469-525 nm), in the Cytation 3® multimodal reader (BioTek®, USA), and the images were captured and analyzed with the Gen5 2.06 program (BioTek®, USA). The experiments were performed five times.

It is observed that treatment with Cur-[G2]-OH promotes the generation of ROS in a concentration-depending manner and is not substantially modified with the use of an antioxidant (NAC), corroborating the lack of response of the Nrf2 pathway. Curcumin treatment was less effective at producing ROS, and its effect is slightly amplified with the use of NAC, suggesting a different mechanism of action from that of Cur-[G2]-OH (FIG. 8).

Effect of Cur-[G2]-OH on Glutathione Concentration

Reduced glutathione (GSH) intracellular concentration were measured by a colorimetric test using the GT10 (Oxford Biomedical Research® kit), following the manufacturer's instructions. $5\times10^5$ C6 cells were seeded in 50 mm Petri dishes (Corning®) and incubated up to a 70% confluence, treated with Cur-[G2]-OH at concentrations of 6, 45, 90 and 300 µM and incubated for 24 hours. The controls were incubated with DMEM media only. Absorbance was read at 400 nm in Cytation3® cell Imaging Multi-mode reader (BioTeck, USA). It is observed that at low concentrations of Cur-[G2]-OH, the synthesis of GSH is induced in C6 cells, but at high concentrations GSH synthesis is inhibited and decrease its concentration in cells.

Example 2

Sensitization of Tumor Cells to Oxidative Stress.

C6 cells ($1\times10^5$ cells/well) were seeded in 96 wells plates. At 24 h, a group of cells were treated with $FeSO_4$ at concentrations of 50, 80, 100 and 150 µM or Cur-[G2]-OH at concentrations of 240 or 300 µM and incubated for an additional 24 hours.

Another group of cells were previously incubated by 2 h with the oxidizing agent $FeSO_4$ at concentrations of 50, 80, 100 and 150 µM and subsequently washed for addition to cur-[G2]-OH at concentrations of 240 or 300 µM, continued to incubate until 24 h was completed. A last group of cells, first was treated with Cur-[G2]-OH at concentrations of 240 or 300 µM for 4 h and subsequently changed the medium and $FeSO_4$ was added to concentrations of 50, 80, 100 or 150 µM continuing incubation for 20 hours more.

The colorimetric test based on the reduction of tetrazolium dye MTT (3-(4,5-dimethyltiazol-2-yl)-2,5-diphenyltetrazolium bromide) was used to determine cell viability (Terry L. et al. Cell Viability Assays. May 1, 2013). The formazan crystals were dissolved with a mixture of isopropanol/acetic acid and the absorbance was measured at 540 nm in a microplate reader (Molecular Devices, Sunnyvale, Calif., USA).

The data were statistically analyzed using a one-way ANOVA analysis, and Newman Keuls post-analysis for multiple comparisons (n=3, Mean=SEM).

It is observed that there is a synergism between Cur-[G-2]-OH and $FeSO_4$, significantly reinforcing the cytotoxicity of both compounds in a concentration-dependent manner, compared to their use separately, but this effect only occurs when cells are pre-incubated with Cur-[G-2]-OH and then subjected to treatment with $FeSO_4$ (FIG. 10).

The invention claimed is:

1. A method for sensitizing multi-resistant tumors characterized by overexpression of the Nrf2 pathway in humans, the method comprising the steps of administering to a patient a medicament comprising a compound Cur-[G-2]-OH of formula:

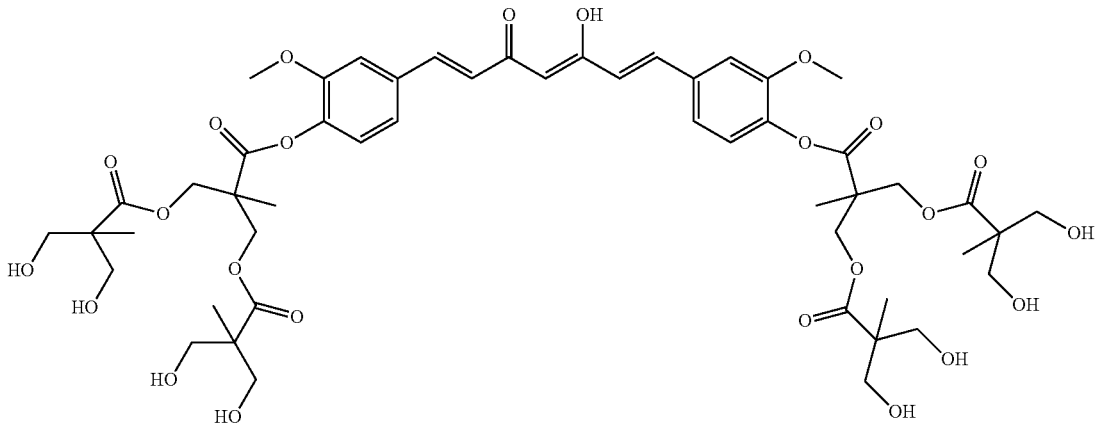 [SMILES: COc1cc(/C=C/C(=O)/C=C(O)/C=C/c2ccc(OC(=O)C(C)(COC(=O)C(C)(CO)CO)COC(=O)C(C)(CO)CO)c(OC)c2)ccc1OC(=O)C(C)(COC(=O)C(C)(CO)CO)COC(=O)C(C)(CO)CO]

wherein the medicament is administered to the patient prior to the administration of an anticancer therapy.

2. The method according to claim 1, wherein the multi-resistant tumor is selected from the group consisting of breast cancer, ovarian cancer, prostate cancer, lung cancer, head and neck cancer, esophagus cancer, colon cancer, metastatic melanoma, hepatocellular carcinoma, and glioblastoma multiforme.

3. The method according to claim 1, wherein the multi-resistant tumor is glioblastoma multiforme.

4. The method according to claim 1, said compound Cur-[G-2]-OH is administered at least 1 hour before pro-oxidant anticancer therapy.

\* \* \* \* \*